US011155403B2

(12) United States Patent
Gugliotti et al.

(10) Patent No.: US 11,155,403 B2
(45) Date of Patent: Oct. 26, 2021

(54) NEEDLE PROTECTOR

(71) Applicant: EMD MILLIPORE CORPORATION, Burlington, MA (US)

(72) Inventors: John Gugliotti, Billerica, MA (US); Michael Gugliotti, Malden, MA (US)

(73) Assignee: EMD Millipore Corporation, Burlington, MA (US)

( * ) Notice: Subject to any disclaimer, the term of this patent is extended or adjusted under 35 U.S.C. 154(b) by 40 days.

(21) Appl. No.: 16/423,464

(22) Filed: May 28, 2019

(65) Prior Publication Data

US 2019/0375578 A1 Dec. 12, 2019

Related U.S. Application Data

(60) Provisional application No. 62/683,306, filed on Jun. 11, 2018.

(51) Int. Cl.
*B65D 85/24* (2006.01)
*B65D 33/16* (2006.01)
*A61M 5/32* (2006.01)

(52) U.S. Cl.
CPC ............ *B65D 85/24* (2013.01); *A61M 5/321* (2013.01); *A61M 5/3202* (2013.01); *B65D 33/16* (2013.01)

(58) Field of Classification Search
CPC .. B65D 33/16; B65D 85/24; A61B 5/150664; A61B 5/150374; A61B 5/150572; A61B 5/150633; A61M 5/321; A61M 5/3213; A61M 5/3216; A61M 5/3205; A61M 5/3202

USPC ................... 206/364, 365, 367, 223
See application file for complete search history.

(56) References Cited

U.S. PATENT DOCUMENTS

| 4,698,057 A | 10/1987 | Joishy |
| 5,615,766 A * | 4/1997 | Gemma, Jr. ...... A61B 17/06061 |
| | | 206/453 |
| 2001/0020152 A1 | 9/2001 | Spinello |
| 2012/0267272 A1* | 10/2012 | Agrawal ............... A61B 50/30 |
| | | 206/363 |

FOREIGN PATENT DOCUMENTS

| CN | 2805772 Y | 8/2006 |
| CN | 2843483 Y | 12/2006 |
| CN | 203647484 U | 6/2014 |
| CN | 204723490 U | 10/2015 |
| CN | 103638583 B | 1/2017 |
| CN | 206792739 U | 12/2017 |
| CN | 206852861 U | 1/2018 |
| DE | 102004059217 A1 | 7/2005 |
| EP | 2659921 B1 | 6/2017 |

(Continued)

*Primary Examiner* — Steven A. Reynolds
(74) *Attorney, Agent, or Firm* — EMD Millipore Corporation

(57) ABSTRACT

A needle protector, having a flexible material, a pocket defining an internal volume, a wrapping strap having a plurality of holes, and a main body disposed between the pocket and the wrapping strap; at least one rigid body or cylinder for placement within the internal volume; and; a pin for placement within one of the plurality of holes, wherein the pin is capable of releasabiy locking the pocket and the main body when the wrapping strap is wrapped around the pocket and the main body.

12 Claims, 4 Drawing Sheets

(56) References Cited

FOREIGN PATENT DOCUMENTS

| | | | |
|---|---|---|---|
| GB | 2361261 | A | 10/2001 |
| GB | 2468945 | A | 9/2010 |
| WO | 2007/022295 | A2 | 2/2007 |

* cited by examiner

NEEDLE PROTECTOR

CROSS-REFERENCE TO RELATED APPLICATION

The present application claims the benefit of priority of U.S. Provisional Application No. 62/683,306, filed Jun. 11, 2018, which is incorporated by reference herein in its entirety.

BACKGROUND

Field

Embodiments of the present disclosure relate to a needle protector and, more particularly, to a size-adjustable sleeve capable of housing and protecting a needle and tubing for storability within an isolator transfer bag or container during shipping and/or storage.

Description of the Related Art

Needles, such as filling needles, are often supplied with isolator transfer bags or bioreactors as part of a fluid transfer set comprising tubing, filters, bags, and various fittings and containers. The filling needles are typically provided with a sheath or cap for enclosing the needle to protect it against contamination, breakage, and bending during handling. The sheath or cap protects the product bags, isolator transfer bags, and containers from being punctured by the filling needles. Also, regulations mandate that an end user is not allowed to touch the filling needles after sterilization so as to prevent contaminants from the user or a user's gloves onto a wetted surface of the filling needle. Otherwise, contaminants could infiltrate the product made within the product bags. However, end users often struggle to keep caps on the filling needles during their installation, handling procedures, and/or have difficulty not contacting the filling needles. Furthermore, some needles, present a propensity to getting damaged during shipping and/or damage the container or bag. Nonetheless, product bags, isolator transfer bags, and containers and needles still become damaged and users still contaminate filling needles. A system that overcomes the foregoing problems would represent an advance in the art

SUMMARY

A needle protector, substantially as shown in and/or described within at least one of the figures, as set forth more completely in the claims and the present disclosure. A storage kit, substantially as shown in and/or described within at least one of the figures, as set forth more completely in the claims and the present disclosure. Various benefits, aspects, novel and inventive features of the present disclosure, as well as details of exemplary embodiments thereof, will be more fully understood from the following description and drawings.

DETAILED DESCRIPTION

Figure 1:
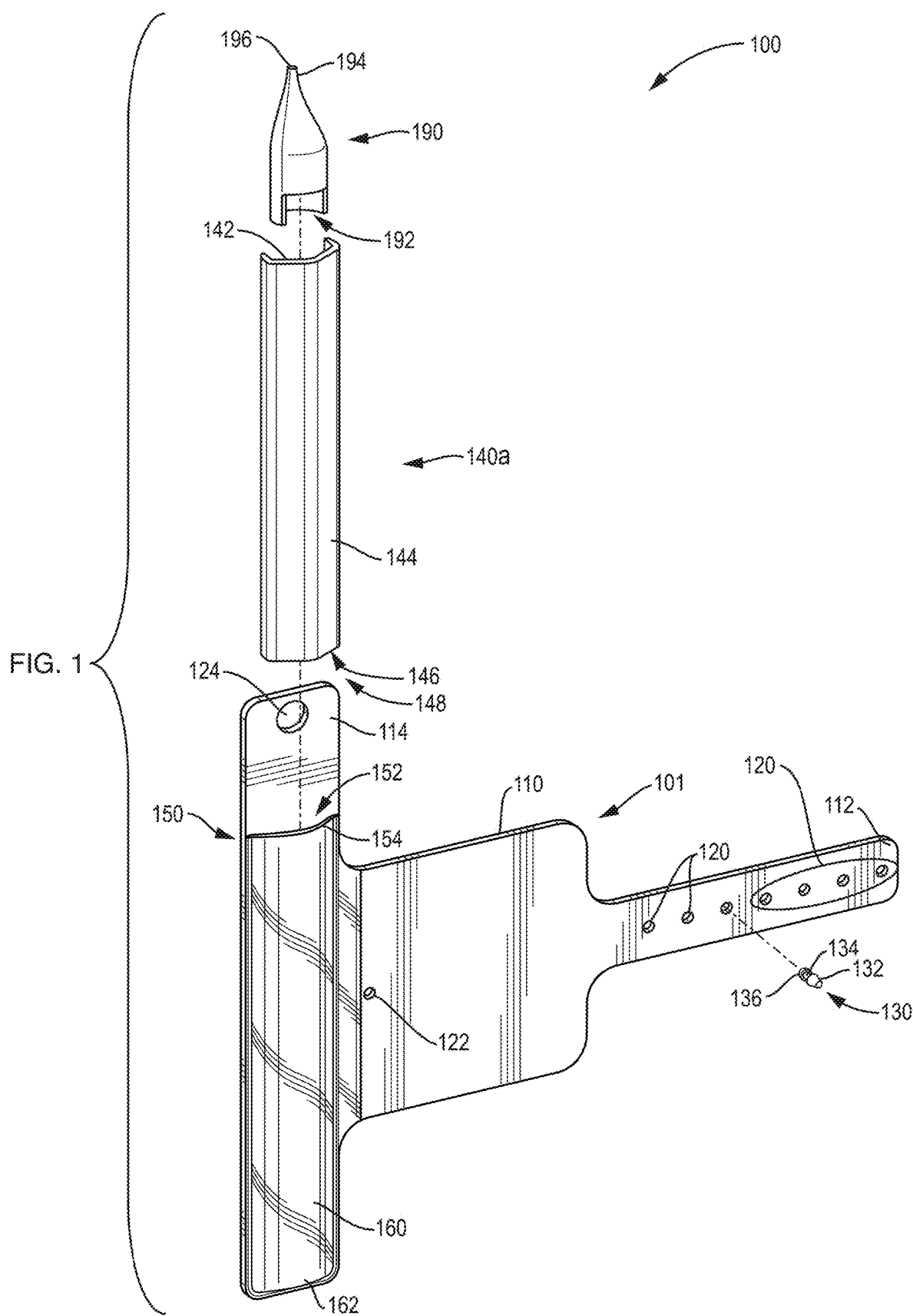
FIG. 1 is a top plan view of a needle protector, according to some embodiments of the disclosure.

So the manner in which the features disclosed herein can be understood in detail, a more particular description of the embodiments of the disclosure, briefly summarized above, may be had by reference to the appended figures. It is to be noted, however, that the appended figures illustrate only typical embodiments of the technologies disclosed herein and are therefore not to be considered limiting of its scope, for the described embodiments may admit to other equally effective embodiments. It is also to be understood that elements and features of some embodiments may be found in some other embodiments without further recitation and that, where possible, identical reference numerals have been used to indicate comparable elements that are common to the figures.

In accordance with some embodiments, the needle protector is designed to receive a needle and be wrapped prior to storage and/or shipping within an isolator transfer bag or other suitable shipping container. In some embodiments, the needle protector is designed to receive a needle having tubing attached thereto and be wrapped prior to storage and/or shipping within an isolator transfer bag or suitable shipping container. In some embodiments, the needle protector further comprises a pocket for housing a rigid body/cylinder into which a needle having tubing attached thereto is placed and wrapped prior to storage and/or shipping within an isolator transfer bag or bag. In some embodiments, the rigid body comprises a U-shape or a truncated U-shaped. In some embodiments, the needle protector further comprises a pocket for housing a rigid body/cylinder into which a needle having tubing attached thereto is placed and wrapped via an adjustable wrapping strap having a plurality of holes and a releasable pin connector, prior to storage and/or shipping within an isolator transfer bag or bioreactor. In some embodiments, the needle protector comprises a hanging hole for hanging while in use. In some embodiments, the needle protector and/or isolator transfer bag or bioreactor comprises monolayer walls or multilayer flexible walls formed of a polymeric composition such as polyurethane, polyethylene, including ultrahigh molecular weight polyethylene, linear low density polyethylene, low density or medium density polyethylene; polypropylene; ethylene vinyl acetate (EVOH); polyvinyl chloride (PVC); polyvinyl acetate (PVA); ethylene vinyl acetate copolymers (EVA copolymers); thermoplastic elastomers (TPE), and/or blends or alloys of any of the foregoing materials as well as other various thermoplastics materials known to those in the art.

The needle protector may be formed by various processes including, but not limited to, co-extrusion of similar or different thermoplastics; multilayered laminates of different thermoplastics; welding and/or heat treatments, heat staking, calendaring, or the like. Any of the foregoing processes may further comprise layers of adhesives, tie layers, primers, surface treatments, and/or the like to promote adhesion between adjacent layers. By "different," it is meant different polymer types such as polyethylene layers with one or more layers of EVOH as well as the same polymer type but of different characteristics such as molecular weight, linear or branched polymer, fillers and the like, are contemplated herein. Any embodiment of the needle protector may comprise medical grade polymers and, in some embodiments, animal-free plastics are used to manufacture the needle protectors. Medical grade polymers may be sterilized, for e.g., by steam, ethylene oxide or radiation, including beta and/or gamma radiation. Also, medical grade polymers are specified for good tensile strength and low gas transfer. In some embodiments, the needle protector comprises a polymeric material and, optionally, is dear or translucent, allowing visual monitoring of the needle, rigid body/cylinder, tubing, tip protector, etc.

Proper design and implementation of the needle protector, needle, needle tip protector, rigid body/cylinder, etc., provides a protection solution across a wide range of needle sizes, tubing diameters and lengths, etc., with the ability to provide improved delivery and storage of the needles and container. Furthermore, the needle protector permits easy packing, unpacking, transit, storage, use, and disposal in an aseptic manner.

FIG. 1 is an upper plan view of a needle protector 100, according to some embodiments of the disclosure. The needle protector 100 comprises a sleeve 101, a rigid body/cylinder 140, and a needle tip protector 190. The sleeve 101 comprises a flexible material, for example, a compliant polymeric film. Some exemplary embodiments of the sleeve 101 comprise a thermoplastic elastomer (TPE), for e.g., a polyurethane material. The sleeve 101 further comprises a pocket 160, which defines an internal volume 152. The sleeve 101 may further comprise a wrapping strap 112. The wrapping strap 112 includes a plurality of holes 120. The sleeve 101 further comprises a main body 110 disposed between the pocket 160 and the wrapping strap 112. The main body 110 optionally comprises a first hole 122. In some embodiments, the first hole 122 houses a releasable locking pin 130. The releasable locking pin 130 can be placed into and removed from the first hole 122 or a plurality of holes 120 repeatedly. In some embodiments, the sleeve 101 has a flange 114 adjacent to an open end 154 of a proximal end 150 of the pocket 160 and opposite a distal end 162 of the pocket 160. In some embodiments, the sleeve 101 comprises a hanging hole 124 disposed within the flange 114.

The needle protector 100 may comprise at least one rigid body/cylinder 140 for placement within the internal volume 152 of the pocket 160. The rigid body/cylinder 140, as depicted, has a first end 144 and a second end 142 distal to the first end 144. The first end 144 of the rigid body/cylinder 140 has an opening 146. A needle (described below) may be placed into the opening 146 in a direction 148. In some embodiments, the second end 142 is open, as depicted or may be closed (not shown). In some embodiments, rigid body or cylinder 140, may be a true cylinder in shape as depicted or may consist of other cross sectional geometries or profiles such as, but not limited to, ovals, diamonds (not shown), and U-shapes. For example, an alternative U-shaped rigid body 140a is depicted. The U-shaped rigid body 140a fits into the pocket 160 much like the rigid body 140. The rigid body or cylinder 140 (or the U-shaped rigid body 140a) is a stiff but compliant plastic so that the rigid body or cylinder 140 can bend slightly during shipping, thereby preventing another failure mode for damaging the needle 170 and/or the isolator transfer bag in which it may be shipped or stored. In some embodiments, the rigid body or cylinder 140 comprises a polymeric material, e.g., polyacetal, polypropylene, polyethylene, polyacrylonitrile-butadiene-styrene) (ABS), nylon 6, or nylon 66 and/or other various polymer materials.

The needle protector 100 may comprise a releasable locking pin 130 for placement within one of the plurality of holes 120, wherein the releasable locking pin 130 is capable of releasably locking the pocket 160 and the main body 110 when the wrapping strap 112 is wrapped around the pocket 160 and the main body 110. The locking pin 130 may be of many designs. As depicted, the locking pin 130 comprises a large head 136, a tapered end 132, and a groove 134. The tapered end 132 can be inserted into at least one of the plurality of holes 120, wherein the large head 136 permits the locking pin 130 to stay housed with the hole 120. When the sleeve 101 is wrapped (depicted below), the locking pin 130 can engage another hole 120, wherein the sleeve 101 becomes releasably wrapped.

The needle protector 100 also comprises a needle point protector 190. The needle point protector 190 comprises a flexible film, i.e., a polymeric film, as described above. The needle point protector 190 comprises an opening 192 for receiving a needle point (described below). The needle point protector 190 may also comprise a tab 194, which is on an end 196 opposite the opening 192. Because the needle point protector 190, as well as the tab 194 are flexible, when inserted into the pocket 160, the pocket 160 is protected from the needle point (shown below). Also, the tab 194 allows the easy and aseptic removal and placement of the needle point protector 190 from or onto the needle. It is to be understood that a user, even when wearing bulky gloves, can remove and place the needle point protector 190 onto a needle without touching the needle point, maintaining a sterile/aseptic condition.

Figure 2:
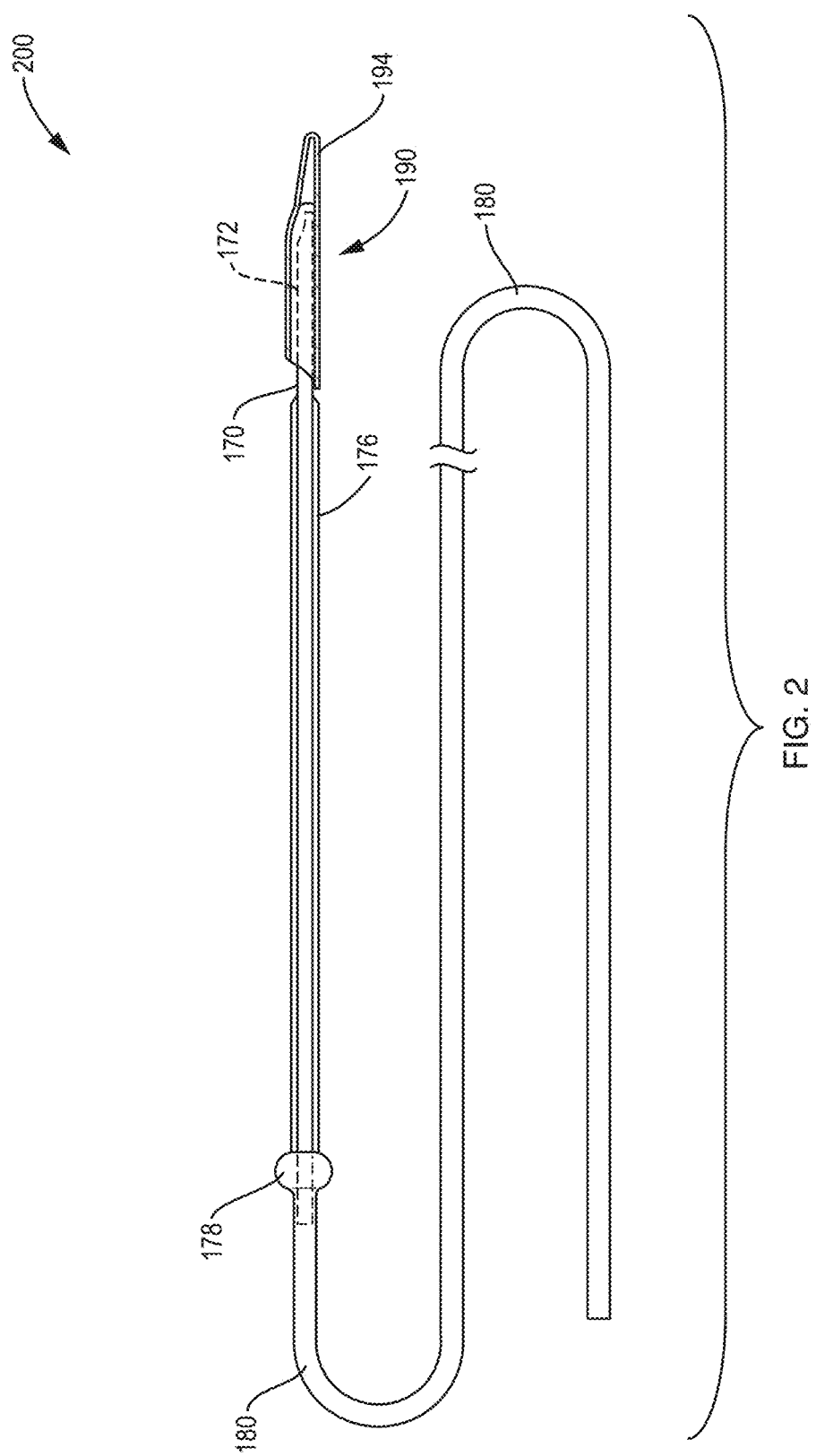
FIG. 2 is a side plan view of a needle and tubing having a needle tip protector disposed on a needle tip, according to some embodiments described in the disclosure.

FIG. 2 is a side plan view 200 of a needle 170 and tubing 180 having a needle tip protector 190 disposed on a needle tip 172, according to some embodiments described in the disclosure. As depicted, the needle 170 also comprises a rigid needle shroud 176 having a shoulder 178. It is to be understood that a rigid needle shroud 176 is optional for any and all embodiments disclosed herein. The tubing 180 can be of various lengths, inner diameters, outer diameters, and polymer types while being capable of being tightly locked/coiled within the sleeve 101, as discussed in greater detail below. Owing to the plurality of holes 120, the sleeve 101 is capable of locking many different lengths and diameters of tubing 180.

Figure 3:
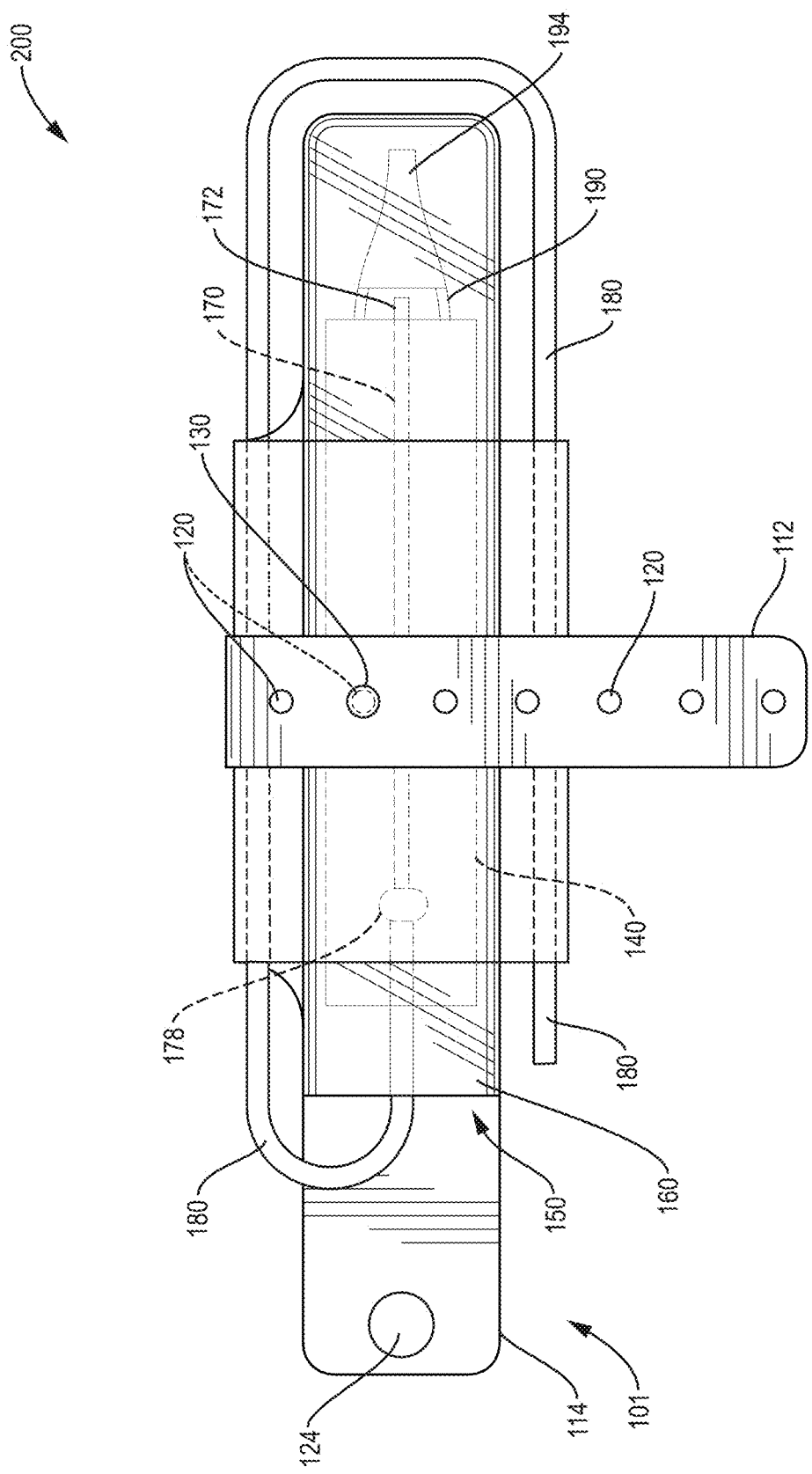
FIG. 3 is a top plan view of a storage kit, according to some embodiments of the disclosure.

FIG. 3 is a top plan view of a storage kit 300, according to some embodiments of the disclosure. The storage kit 300 comprises the needle 170, wherein the needle 170 has the needle tip 172. The needle tip 172 is disposed within the needle tip protector 190, wherein the needle tip protector 190 comprises, optionally, the tab 194. The needle 170 and the needle tip protector 190 are disposed within the rigid body or cylinder 140. In some embodiments, the rigid body or cylinder 140 has an inner diameter that is slightly smaller than an outer diameter of the shoulder 178, creating an interference fit, thereby promoting a secure fit during shipping and/or storage. The rigid body or cylinder 140 is disposed within the pocket 160 of the sleeve 101.

As depicted, the storage kit 300 is in a state for storage. Specifically, the tubing 180 is coiled, bundled, or otherwise folded so that the body 110 of the sleeve 101 is wrapped about the tubing 180 when the sleeve 101 is rolled. And, the wrapping strap 112 wraps the body 110 and the tubing 180. For the sake of clear drawings, some of the tubing 180 is omitted. The storage kit 300 is releasably locked by the locking pin 130, which is disposed within one of the plurality of holes 120 and is engaged within another of the plurality of holes 120.

Figure 4:
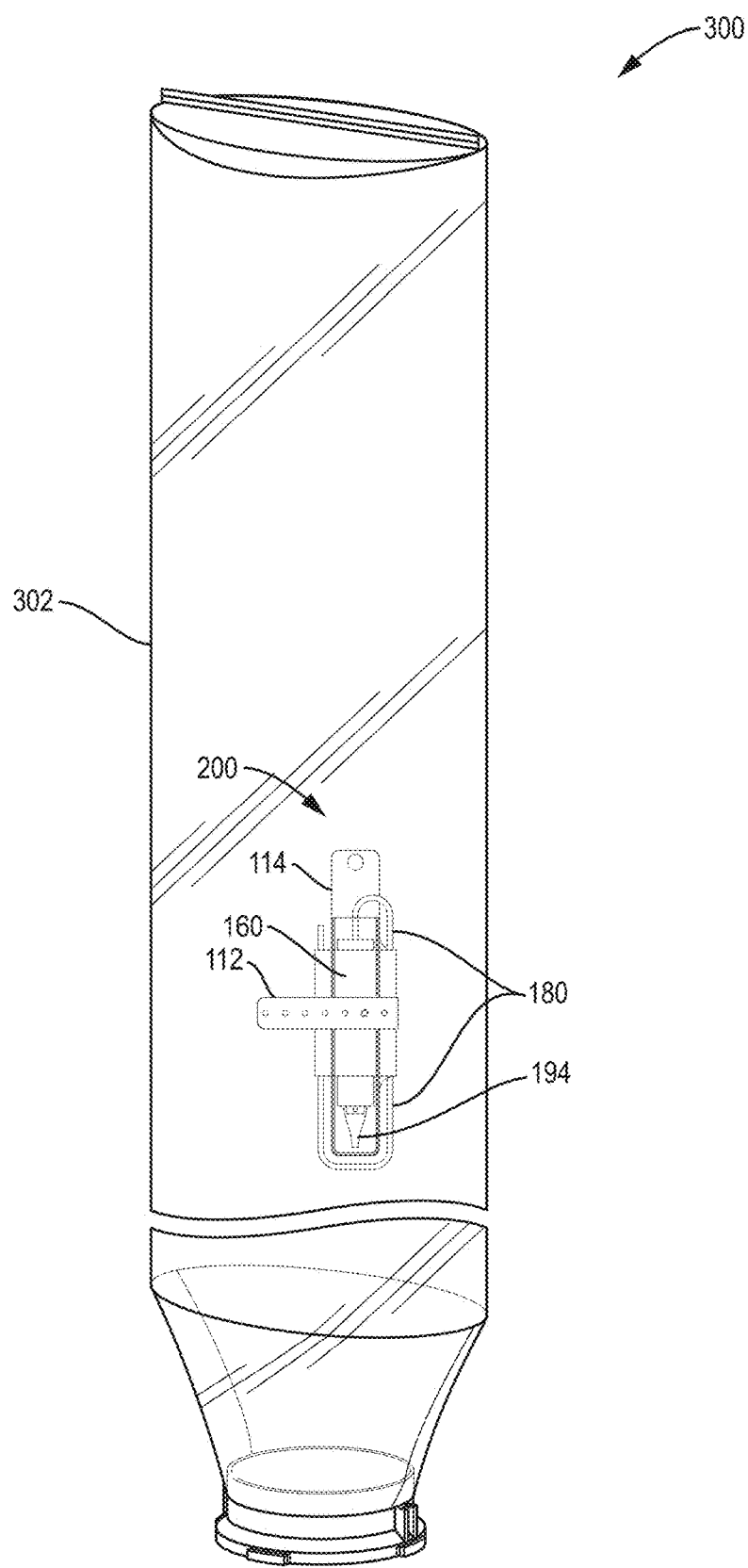
FIG. 4 is a side plan view of the needle protector of FIGS. 1-2 and the storage kit of FIG. 3 inside a bag, according to embodiments of the disclosure.

As shown, the sleeve 101 is used to ensure not only the safe shipping and handling of the needles 170 within an isolator transfer bag or suitable shipping container (not shown), but also to improve the user's interaction with the needle protector 100 and storage kit 300. The needle tip protector 190 provides protection throughout the user handling procedures. The rigid body or cylinder 140 ensures that the needle 170 is protected during shipment. The wrapping strap 112 enables easy organized bundling of the tubing 180 attached to the needle 170. Also, the rigid body or cylinder 140 permits the needle 170 and the tubing 180 to be wrapped tightly with the wrapping strap 112, while protecting the needle 170 from bending and protecting the sleeve 101 from damage that might be caused by the needle 170. The needle tip protector 190 prevents the user from inadvertently touching the needle 170 after the needle 170 has been sterilized, which prevents contaminants from infiltrating, for example, the product made in the isolator transfer bag or bioreactor (not shown) as are known to those in the at The needle tip protector 190 is light and tight enough to allow the needle 170 to remain covered during the handling process. The tip protector 190 may be of a variable length so a portion of the needle 170, up to the entire needle 170, is covered. Also, long lengths of tubing 180 can be accommodated by the sleeve 101 and the plurality of holes 120 to prevent the tubing 180 from becoming tangled during manufacture and shipment. The use of a button-like locking pin 130 for securing the wrapping strap 112 permits the handling of needles within restricted Class A areas where large bulky gloves are required to install the needles into fillers. The wrapping strap 112 and locking pin 130 design allows for easier release of the tubing 180 compared previous wraps and/or adhering methods. In addition, by incorporating the plurality of holes 120, which may be of variable sizes in any or all embodiments into the sleeve 101, waste or contamination is reduced. Furthermore, wire tie style wraps, which would otherwise be necessary, cannot, therefore, be left behind or lodged in the equipment. The incorporation of a hanger hole 124 adjacent and above the needle allows the needle 170, tubing 180, and sleeve 101 to be hung by the user in or on equipment, as opposed to hanging by the needle 170 or the tubing 180 attached to the needle 170. Moreover, the hanger hole 124 in the sleeve places the weight of the storage kit 300 from the tubing 180 to the sleeve 101, permitting a safer manner of handling the needle 170. FIG. 4 is a side plan view of the needle protector 100, as shown in FIGS. 1-2 and the storage kit 300, as shown in FIG. 3 inside a bag 302, such as an isolator bag, according to embodiments of the disclosure. As shown, the flange 114, the tab 194, and the pocket 160, wherein the tubing 180 is wrapped by the wrapping strap 112.

All ranges for formulations recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the, recited order of magnitude or one lower. For example, 3 or more includes 4, or 3.1 or more.

Reference throughout this specification to "one embodiment," "certain embodiments," "one or more embodiments," "some embodiments," or "an embodiment" indicates that a feature, structure, material, or characteristic described in connection with the embodiment is included in at least one embodiment of the disclosure. Therefore, the appearances of the phrases such as "in one or more embodiments," "in certain embodiments," "in one embodiment," "some embodiments," or "in an embodiment" throughout this specification are not necessarily referring to the same embodiment.

Although some embodiments have been discussed above, other implementations and applications are also within the scope of the following claims. Although the specification describes, with reference to particular embodiments, it is to be understood that these embodiments are merely illustrative of the principles and applications of the present disclosure. It is therefore to be further understood that numerous modifications may be made to the illustrative embodiments and that other arrangements and patterns may be devised without departing from the spirit and scope of the embodiments according to the disclosure. Furthermore, particular features, structures, materials, or characteristics may be combined in any suitable manner in any one or more of the embodiments.

Publications of patent applications and patents and other non-patent references, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A needle protector made of a flexible material, comprising:
    a pocket defining an internal volume, a wrapping strap having a plurality of holes, and a main body disposed between the pocket and the wrapping strap, wherein the pocket comprises a longitudinal axis, the main body extending from the pocket and the wrapping strap extending from the main body;
    at least one rigid body or cylinder for placement within the internal volume; and;
    a locking pin for placement within one of the plurality of holes, wherein the locking pin is capable of releasably locking the pocket and the main body when the wrapping strap is wrapped around the pocket and the main body.

2. The needle protector of claim 1, further comprising a hanging hole that is disposed adjacent to at least one of the pocket or the main body.

3. The needle protector of claim 1, a wherein the rigid body disposed within the internal volume of the pocket is U-shaped.

4. A storage kit made of a flexible material, comprising;
    a needle protector comprising a pocket, a wrapping strap having a plurality of holes, a main body disposed between the pocket and the wrapping strap;
    a locking pin disposed within at least one of the plurality of holes of the wrapping strap;
    a needle having a needle tip disposed on a first end of the needle;
    tubing connected to a second end of the needle, opposite the first end of the needle;
    a flexible needle tip protector; and
    a rigid body or cylinder suitable for placement within the pocket, wherein the flexible tip protector is disposed on the needle tip and wherein the flexible tip protector and needle tip are placed within the rigid body or cylinder and placed into the pocket and wherein the tubing is coiled; the wrapping strap is then wrapped around the coiled tubing and the pocket; and the wrapping strap is locked with the locking pin being disposed within the at least one of the plurality of holes.

5. The storage kit of claim 4, wherein the wrapping strap contains between three and seven holes spaced apart from one another.

6. The storage kit of claim 4, wherein the pocket is closed on a distal end.

7. The storage kit of claim 4, wherein the pocket is open on a proximal end and adjacent to a hanging hole.

8. The storage kit of claim 4, wherein the main body comprises a first hole adjacent to the pocket.

9. The storage kit of claim 4, wherein the rigid body or cylinder is open on a first end and a second end for accommodating needles of variable lengths.

10. The storage kit of claim 4, wherein the needle protector comprises a flexible polymeric material.

11. A method of storing a needle within a needle protector of claim 1 and a collapsible container, comprising:
    providing a collapsible container defining a working volume;
    placing a needle having a needle tip on a first end and tubing disposed on a second end into a needle tip protector, wherein the needle tip protector comprises a flexible polymeric material,
    placing the needle and needle tip protector into the rigid body or cylinder;
    placing the rigid body or cylinder into the pocket of the needle protector;
    coiling the tubing;
    wrapping the tubing and the pocket with the wrapping strap;
    releasably locking the wrapping strap with the locking pin; and
    placing the locked needle protector into the working volume of the collapsible container.

12. The method of claim 11, wherein said collapsible container is an isolator transfer bag.

\* \* \* \* \*